(12) United States Patent
Masters et al.

(10) Patent No.: US 8,847,718 B2
(45) Date of Patent: *Sep. 30, 2014

(54) ROTARY TRANSFORMER

(71) Applicant: Boston Scientific SciMed, Inc., Maple Grove, MN (US)

(72) Inventors: Donald Masters, San Diego, CA (US); Stuart L. Carp, Menlo Park, CA (US); Peter Thornton, Los Altos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 64 days.

This patent is subject to a terminal disclaimer.

(21) Appl. No.: 13/769,062

(22) Filed: Feb. 15, 2013

(65) Prior Publication Data

US 2013/0154779 A1 Jun. 20, 2013

Related U.S. Application Data

(63) Continuation of application No. 11/961,912, filed on Dec. 20, 2007, now Pat. No. 8,378,771.

(51) Int. Cl.
| | |
|---|---|
| H01F 21/00 | (2006.01) |
| H01F 38/18 | (2006.01) |
| H01F 21/06 | (2006.01) |
| A61B 8/00 | (2006.01) |
| A61B 8/12 | (2006.01) |
| H01F 27/02 | (2006.01) |

(52) U.S. Cl.
CPC .............. *H01F 21/06* (2013.01); *H01F 38/18* (2013.01); *A61B 2562/227* (2013.01); *A61B 8/4461* (2013.01); *H01F 27/02* (2013.01); *A61B 8/12* (2013.01)
USPC ........... 336/131; 600/459; 600/462; 600/585; 604/109; 604/165.04

(58) Field of Classification Search
USPC .......... 600/459, 462–465, 585; 604/108, 109, 604/165.04; 310/46–48; 323/328–348; 336/130–136
See application file for complete search history.

(56) References Cited

U.S. PATENT DOCUMENTS

| | | | |
|---|---|---|---|
| 3,070,660 | A | 12/1962 | Ippolito |
| 4,041,541 | A | 8/1977 | Frossard et al. |

(Continued)

FOREIGN PATENT DOCUMENTS

| | | |
|---|---|---|
| WO | 9216147 A1 | 10/1992 |
| WO | 9629934 A1 | 10/1996 |
| WO | 0024448 A2 | 5/2000 |

OTHER PUBLICATIONS

U.S. Appl. No. 11/961,912, Official Communication mailed Oct. 18, 2011.

(Continued)

*Primary Examiner* — Parikha Mehta
(74) *Attorney, Agent, or Firm* — Lowe Graham Jones PLLC; Bruce E. Black

(57) ABSTRACT

Described herein are rotary transformers for coupling signals between components that rotate relative to one another. In an exemplary embodiment, a rotary transformer comprises a rotary shaft, a first magnetic core on the rotary shaft, and a first winding wound around the first magnetic core. The rotary transformer further comprises a hollow second magnetic core, and a second winding wound along the inner wall of the second magnetic core. During operation, the first winding on the rotary shaft rotates within the second winding with the magnetic cores magnetically coupling signals between the two windings. Also, the first and second windings are closely spaced to provide capacitive coupling between the windings that extends the frequency response of the transformer. In one embodiment, the windings comprises substantially flat conductors wound in the shape of the windings. In another embodiment, each of the windings comprises circular loops connected by jogs.

20 Claims, 7 Drawing Sheets

(56) References Cited

U.S. PATENT DOCUMENTS

| | | |
|---|---|---|
| 4,149,419 A | 4/1979 | Connell, Jr. et al. |
| 4,674,515 A | 6/1987 | Andou et al. |
| 4,677,853 A | 7/1987 | Kawabuchi |
| 4,748,985 A | 6/1988 | Nagasaki |
| 4,773,426 A | 9/1988 | Molnar et al. |
| 4,869,257 A | 9/1989 | Molnar et al. |
| 4,880,011 A | 11/1989 | Imade et al. |
| 4,936,307 A | 6/1990 | Saito et al. |
| 4,989,582 A | 2/1991 | Sakiyama et al. |
| 5,022,383 A | 6/1991 | Sakiyama et al. |
| 5,168,878 A | 12/1992 | Takano |
| 5,243,988 A | 9/1993 | Sieben et al. |
| 5,313,950 A | 5/1994 | Ishikawa et al. |
| 5,353,798 A | 10/1994 | Sieben |
| 5,438,997 A | 8/1995 | Sieben et al. |
| 5,445,155 A | 8/1995 | Sieben |
| 5,544,660 A | 8/1996 | Crowley |
| 6,333,581 B1 | 12/2001 | Kohl et al. |
| 6,641,546 B2 | 11/2003 | White et al. |
| 2001/0029337 A1 | 10/2001 | Pantages et al. |
| 2002/0193690 A1 | 12/2002 | Moore et al. |
| 2009/0295523 A1 | 12/2009 | Schwander et al. |

OTHER PUBLICATIONS

U.S. Appl. No. 11/961,912, Official Communication mailed Feb. 27, 2012.

U.S. Appl. No. 11/961,912, Official Communication mailed May 23, 2012.

U.S. Appl. No. 11/961,912, Official Communication mailed Nov. 15, 2012.

ROTARY TRANSFORMER

CROSS-REFERENCE TO RELATED APPLICATIONS

This patent application is a continuation of U.S. patent application Ser. No. 11/961,912 filed on Dec. 20, 2007, which issued as U.S. Pat. No. 8,378,771 on Feb. 19, 2013, which is incorporated herein by reference.

FIELD OF THE INVENTION

The present invention relates to catheter systems, and more particularly to rotary transformers for coupling electrical signals in catheter systems.

BACKGROUND INFORMATION

Rotary transformers are used in catheter systems to couple electrical signals between rotating and non-rotating components of the catheter systems. For example, a catheter system may comprise a rotatable transducer received within a catheter body. The transducer is attached to the distal end of a drive cable that is driven by a motor to rotate the transducer within the catheter body. In this example, a rotary transformer may be used to couple electrical signals between the rotating transducer and stationary electronics.

A rotary transformer typically comprises two ferrite cores, in which one of the cores rotates relative to the other core. A primary winding is wound around one core and a secondary windings is wound around the other core. The two cores provide magnetic coupling between the two windings, thereby coupling electrical signals from one winding to the other winding.

A problem with existing rotary transformers is that their magnetic coupling degrades at high frequencies. This causes the amplitude of signals coupled through the rotary transformer to roll off at high frequencies, thereby limiting the bandwidth of the rotary transformer.

Therefore, there is a need for rotary transformers that are able to couple signals at higher frequencies. There is also a need for rotary transformers having wider bandwidths.

SUMMARY OF THE INVENTION

The present invention provides rotary transformers for coupling signals between components that rotate relative to one another.

In an exemplary embodiment, a rotary transformer comprises a rotary shaft, a first magnetic core on the rotary shaft, and a first winding wound around the first magnetic core. The rotary transformer farther comprises a hollow second magnetic core, and a second winding wound along the inner wall of the second magnetic core. The rotary shaft, first magnetic core and first winding are located within the second magnetic core and second winding. During operation, the first winding on the rotary shaft rotates within the second winding. The first and second magnetic cores magnetically couple signals between the two windings. Further, the first and second windings are closely spaced to provide capacitive coupling between the two windings. The capacitive coupling extends the frequency response of the rotary transformer by providing a low impedance conduction path between the two windings at high frequencies.

In one exemplary embodiment, each of the windings comprises a substantially flat strip conductor wound in the shape of the winding. In this embodiment, the first and second windings are aligned to form a parallel-plate capacitor comprising closely spaced parallel plates (i.e., the conductors of the first and second windings). The close spacing between the flat strip conductors of the first and second windings provides a large capacitive coupling and tight magnetic coupling that extend the bandwidth of the transformer.

In another exemplary embodiment, each of the windings comprises circular loops connected by jogs. In this embodiment, the circular loops of the first winding are aligned with the circular loops of the second winding. An advantage of this embodiment is that the overlap of the circular loops of the two windings does not change during rotation of the first winding. As a result, the capacitive coupling between the two windings remains substantially constant during rotation, which prevents unwanted amplitude modulation from being introduced into the coupled signal.

In another exemplary embodiment, each of the windings comprises a substantially flat strip conductor wound into a helical shape.

In another exemplary embodiment, each of the windings is fabricated by cutting or etching a hollow cylindrical piece into the shape of the respective winding. In one embodiment, the first winding and/or second winding are thinned down to obtain the desired gap between the windings. Thinning down the windings to the desired gap provides precise control of the gap size without requiring tight tolerances on the magnetic cores. This is advantageous because the cores may be made of brittle ferrite material, which is difficult to machine.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES in order to better appreciate how the above-recited and other advantages and objects of the present inventions are objected, a more particular description of the invention briefly described above will be rendered by reference to specific embodiments thereof, which are illustrated in the accompanying drawings, it should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION

Figure 1:
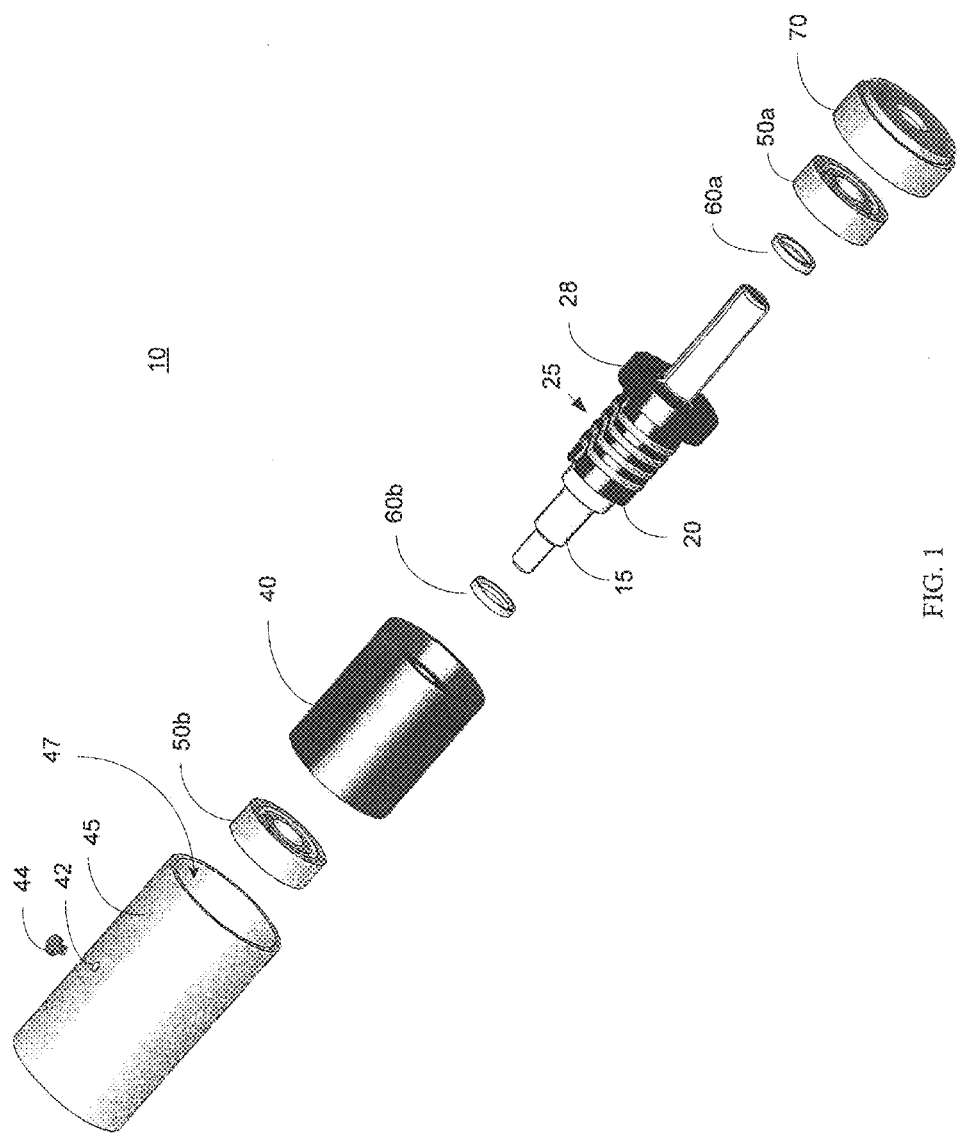
FIG. 1 shows an exploded view of a rotary transformer according to an example embodiment of the present invention.
Figure 2:
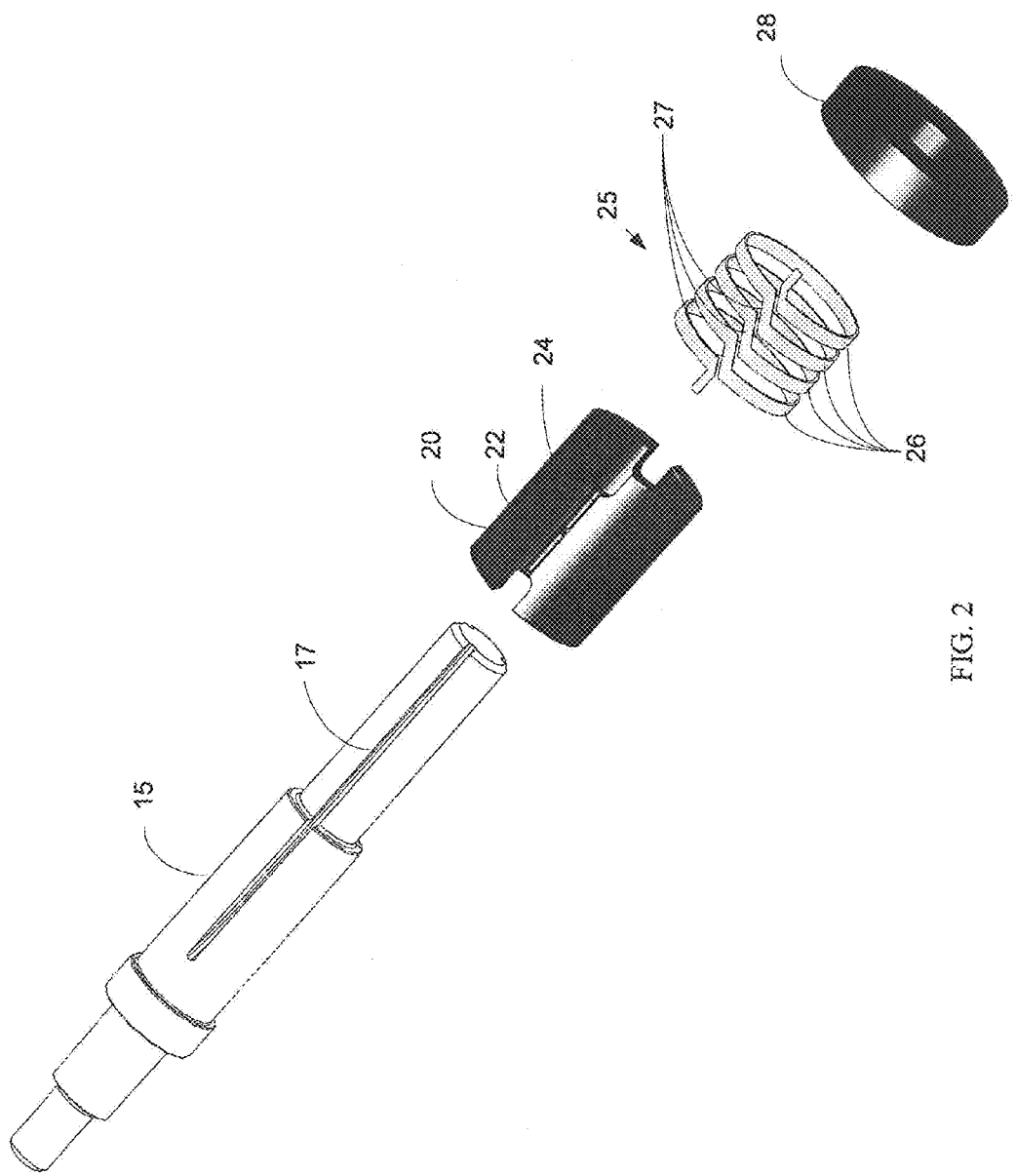
FIG. 2 shows an exploded view of rotating components of the rotary transformer according to an example embodiment of the present invention.
Figure 3:
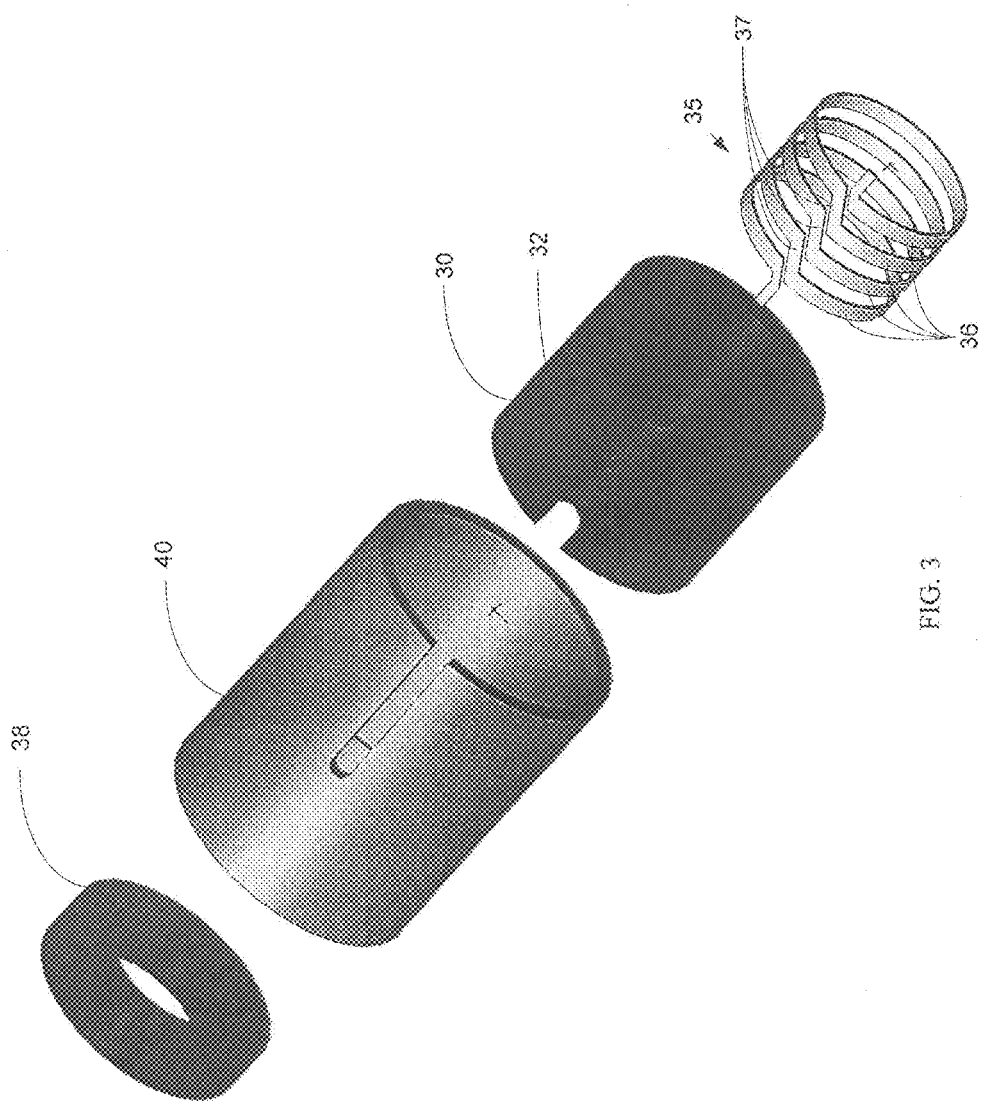
FIG. 3 shows an exploded view of non-rotating parts of the rotary transformer according to an example embodiment of the present invention.

FIGS. 1-3 show exploded views of a rotary transformer 10 according to an exemplary embodiment of the present invention. The rotary transformer 10 comprises a rotary shaft 15, a first magnetic core 20 e.g., ferrite core, disposed on the rotary shaft 15, and a first winding 25 wound around the first magnetic core 20, as best shown in FIG. 2. The rotary shaft 15 includes grooves 17 for running wires (not shown) or other conductors to the first winding 25, in a preferred embodiment, the first winding 25 comprises a substantially flat strip conductor wound around the first magnetic core 20.

The rotary transformer further 10 comprises a second magnetic core 30 and a second winding 35 within the second magnetic core 30, as best shown in FIG. 3. In a preferred embodiment, the second winding 35 comprises a substantially flat strip conductor wound along the inner wall of the second magnetic core 30. The rotary shaft 15, the first magnetic core 20 and the first winding 25 are disposed within the second magnetic core 30 and the second winding 35. In the assembled rotary transformer 10 (shown in FIG. 4), the first winding 25 rotates within the second winding 35. The rotary transformer 10 further comprises a nonconductive case 40 and a metal housing 45. The magnetic cores 20, 30, windings 25, 35 and rotary shaft 15 are all housed within the metal housing 45. The second magnetic core 30 is disposed within the nonconductive case 40 to electrically isolate the second magnetic core 30 from the metal housing 45. The case 40 may be made of ceramic, plastic, or other nonconductive material. The two windings 25, 35 may be made of copper, brass, or other conductive material. In an embodiment, each winding is fabricated by cutting or etching a cylindrical metal piece into the shape of the winding, as described further below.

Figure 4:
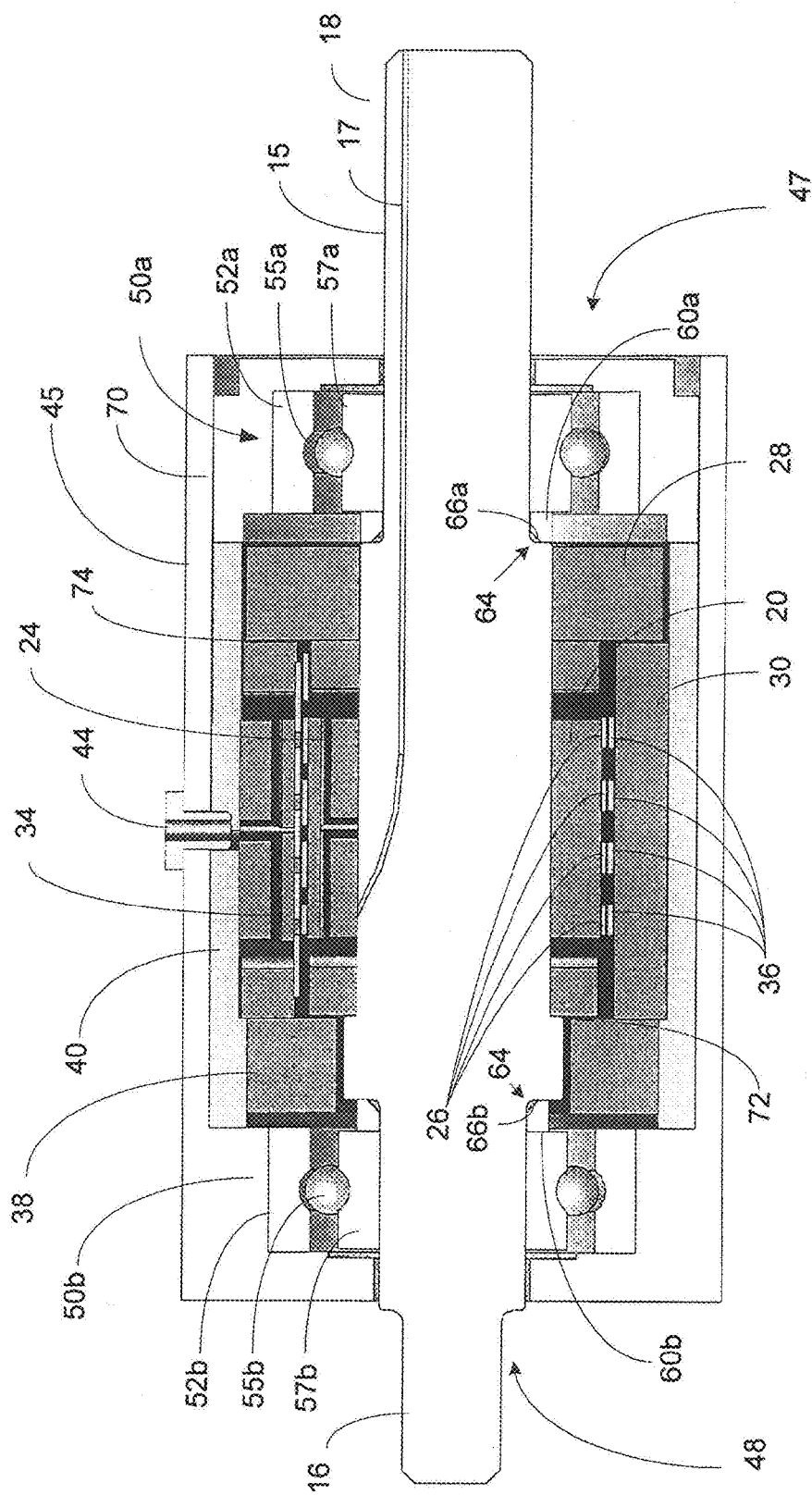
FIG. 4 shows a cross-sectional view of the rotary transformer according to an example embodiment of the present invention.

The rotary transformer 10 also comprises two ball bearings 50a, 50b on either side of the rotary shaft 15 and housed within the housing 45. The rotary shaft 15 passes through the ball bearings 50a, 50b which facilitate rotation of the rotary shaft 15 within the housing 45. FIG. 4 shows a cross-sectional view of the ball bearings 50a, 50b in the assembled rotary transformer 10, in which each ball bearing 50a, 50b comprises hearing halls 55a, 55b sandwiched between a stationary member 52a, 52b and a rotating member 57a, 57b around the rotary shaft 15. The rotary transformer 10 further comprises two alignment rings 60a, 60b on either side of the first magnetic core 20 on the rotary shaft 15 for aligning the first winding 25 with respect to the second winding 35, as explained further below. As shown in FIG. 4, the alignment rings 60a, 60b abut side walls of the rotary shaft 15. The rotary shaft has curved corners 64 between the side walls and longitudinal surfaces of the rotary shaft 15. The curved corners 64 reduce stress at the transition between the side walls and the longitudinal surfaces of the rotary shaft 15, thereby preventing cracking of the rotary shaft 15 due to stress. Each alignment ring 60a, 60b has a chamfer or beveled edge 66a, 66b facing the respective curved corner 64 of the rotary shaft 15 to accommodate the curved corner 64.

The rotary transformer 10 further comprises a first magnetic core end 28 on the rotary shaft 15 and abutting the first magnetic core 20. In the exemplary embodiment shown in FIGS. 1-4, both the first magnetic core 28 and first magnetic core end 28 are cylindrical with the first magnetic core end 28 having a larger outer diameter than the first magnetic core 20.

The first magnetic core end 28 rotates with the first magnetic core 20 on the rotary shaft 15. The rotary transformer 10 also comprises a second magnetic core end 38 abutting the second magnetic core 30. In the exemplary embodiment shown in FIGS. 1-4, both the second magnetic core 30 and second magnetic core end 38 are cylindrical with the second magnetic core end 38 having a smaller inner diameter than the second magnetic core 30. The second magnetic core end 38 is stationary with respect to the second magnetic core 30. Both the first and second magnetic core ends 28, 38 may be made of the same ferrite material as the first and second magnetic cores 20, 30. As shown in FIG. 4, the first and second magnetic cores 20, 30 are located between the first and second magnetic core ends 28, 38 within the housing 45. The first and second magnetic core ends 28, 38 enhance the magnetic coupling provided by the first and second magnetic cores 20, 30 by directing magnetic flux from the sides of the one of the cores 20, 30 to the sides of the other core 20, 30. To facilitate rotation of the rotary shaft 15 within the housing 45, the first magnetic core 20 and the second magnetic core end 38 are separated by a small air gap 72 and the second magnetic core 30 and the first magnetic core end 28 are separated by a small air gap 74. In other exemplary embodiments, the first and second core ends 28, 38 may both be on the rotary shaft 16 and rotate with the first magnetic core 20, or both magnetic cores ends 28, 38 may be stationary with respect to the second magnetic core 30.

As shown in FIGS. 1 and 4, the housing 45 comprises a first opening 47 and a smaller second opening 48. During assembly, the ball bearings 50a, 50b, case 40, magnetic cores 20, 30, magnetic core ends 28, 38 and rotary shaft 15 are placed inside the housing 45 through the first opening 47. The rotary transformer 10 further comprises a cap 70 that is fitted in the first opening 47 to hold the ball bearings 50a, 50b, case 4S, magnetic cores 20, 30, magnetic core ends 28, 38 and rotary shaft 15 in the housing 15. One of the ball bearings 50a is housed within the cap 70. One end 16 of the rotary shaft 15 passes through the second opening 48 of the housing 45 while the other end 18 of the rotary shaft 15 passes through an opening in the cap 70.

As shown in FIG. 4, the first magnetic core 20 includes channels 24 for connecting wires (not shown) from a rotating element, e.g., transducer, to the first winding 25. The wires for the first winding extend along the grooves 17 in the rotary shaft 15 to the rotating element. The wires enter the channels 24 from the rotary shaft 15 through a hole 22 in the first magnetic core 20 (shown in FIG. 2). An example where the rotating element is a transducer is given below. Similarly, the second magnetic core 30 includes channels 34 for connecting wires (not shown) from the second winding 35 to stationary electronics (not shown). The wires for the second windings 35 exit the second magnetic core 30 through a hole 32 (FIG. 3). These wires exit the housing 45 through a hole 42 in the housing 45.

The first winding 25 will now be described in greater detail with reference to FIG. 2. In a preferred embodiment, the first winding 25 comprises a plurality of circular loops 26 with jogs 27 connecting adjacent loops 26. Each circular loop 26 has a small gap where jogs 27 connect the circular loop 26 to adjacent circular loops 26. The first winding 25 includes two ends for connecting wires to the first winding 25. As shown in FIG. 3, the second winding 35 has a similar shape as the first winding 25 with a slightly larger diameter to allow the first winding 25 to rotate within the second winding 35. The second winding 35 comprises a plurality of circular loops 36 with jogs 37 connecting adjacent loops 36.

As shown in FIG. 4, the first and second windings 25, 35 are positioned within the housing 45 such that the circular loops 26, 36 of the first and second windings 25, 35 are aligned with each other. This alignment is adjusted by the widths of the alignment rings 60a, 60b. The first winding 25 rotates within the second winding 35 and is separated from the second winding 35 by a small space or gap. Because of the alignment and close spacing between the first and second windings 25, 35, the first and second windings 25, 35 act as a capacitor that provides capacitive coupling between the first and second windings 25, 35. In the preferred embodiment, each of the first and second windings 25, 35 comprises flat strip conductors wound into the respective winding. As a result, the first and second windings act as a parallel-plate capacitor comprising parallel plates (i.e., the conductors of the first and second windings) separated by the space between the first and second windings 25, 35.

During operation, the magnetic cores 20, 30 provide magnetic coupling between the first and second windings 25, 35 at low frequencies, which couples electrical signals between the windings 25, 35. At higher frequencies, the magnetic coupling between the first and second windings 25, 35 degrades. The capacitive coupling between the first and second windings 25, 35 provides a low impedance conduction path between the first and second windings 25, 35 at higher frequencies. Thus, the capacitive coupling provides coupling of electrical signals between the windings 25, 35 at higher frequencies, thereby extending the frequency response of the rotary transformer 10 beyond that provided by the magnetic coupling. As a result, the rotary transformer 10 is able to couple signals over a wider bandwidth.

Variations in the capacitive coupling between the windings 25, 35 during rotation can introduce unwanted amplitude modulation into the signal being coupled between the windings 25, 35. This amplitude modulation is a type of signal distortion. In the embodiment shown in FIGS. 1-4, the overlap of the circular loops 26, 36 of the first and second windings 25, 36 does not change as the first winding 25 rotates within the second winding 35. As a result, the capacitive coupling provided by the overlap of the circular loops 26, 36 of the first and second windings 25, 35 is substantially constant and independent of the angular position of the first winding 25. Therefore, the circular loops 26, 36 reduce amplitude modulation due to variations in the capacitive coupling during rotation.

Figure 5:
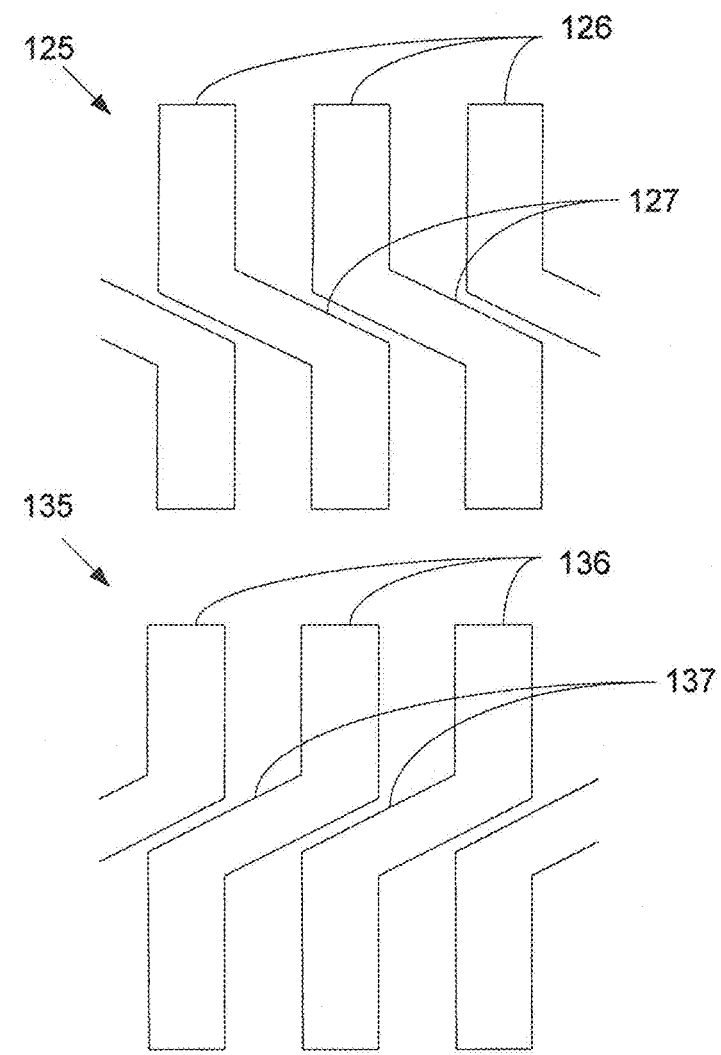
FIG. 5 shows windings of a rotary transformer according to an example embodiment of the present invention.

The jogs 27, 37 of the first and second windings 25, 35 cause variations in the capacitive coupling between the first and second windings 25, 35 during rotation. However, these variations only occur for short time intervals when the jogs 27, 37 of the first and second windings 25, 35 overlap. Most of the time during rotation, the jogs 27, 37 do not overlap, and therefore do not contribute to capacitive coupling between the windings 25, 35. Further, these variations can be minimized by making the jogs 27, 37 much smaller than the circular loops 26, 36. To further reduce variations in the capacitive coupling caused by the jogs 27, 37, the jogs of the first and second windings can be angled in different directions. An example of this is illustrated in FIG. 5, which shows side-by-side top views of the first winding 125 and second winding 135 according to an exemplary embodiment. The jogs 127, 137 of the first and second windings 126, 136 are at different angles, which reduces the overlap between the jogs 127, 137, and hence variations in the capacitive coupling caused by the overlap of the jogs 127, 137.

Figure 6:
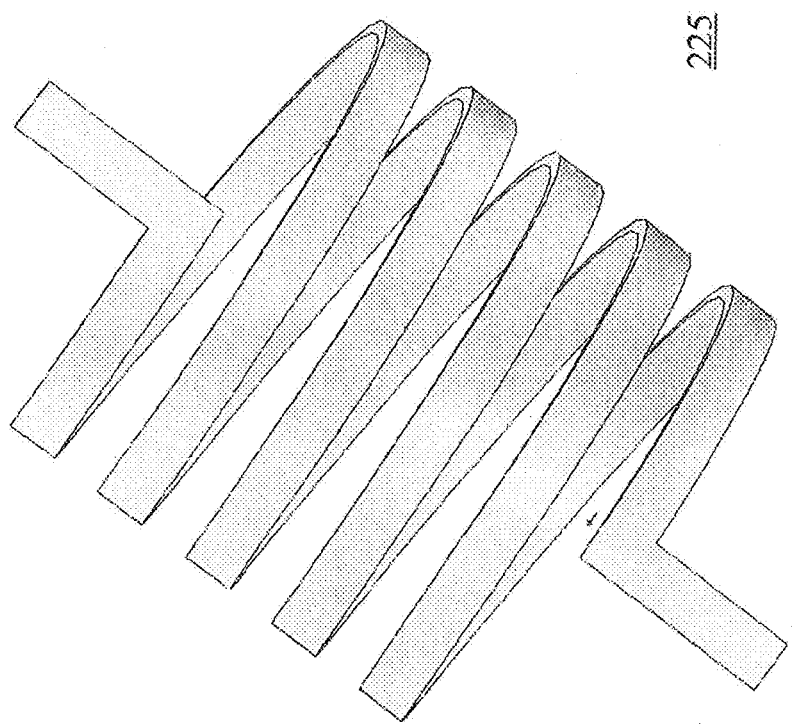
FIG. 6 shows a winding of a rotary transformer according to an example embodiment the present invention.

FIG. 6 shows the first winding 225 according to another exemplary embodiment of the present invention. In this embodiment, the first winding 225 comprises a flat strip conductor wound in a helical shape around the magnetic core (not shown). The second winding (not shown) is similarly wound in a helical shape with a slightly larger diameter than the first winding to allow the first winding to rotate within the second winding. A drawback of this embodiment is that the overlap between the two helical windings varies as the first helical winding rotates within the second helical windings. As a result, the capacitive coupling between the two windings varies during rotation causing amplitude modulation in the signal being coupled between the windings. The rate of the amplitude modulation is a function of the rate of rotation of the first winding. However, the amplitude modulation can be estimated based on the rate of rotation of the first winding, and the shape of the windings. The estimated amplitude modulation can be used by signal processing software or firmware to remove the amplitude modulation from the coupled signal.

Methods for fabricating rotary transformers will now be given. In a preferred embodiment, the first winding is fabricated from a hollow cylindrical piece of conducting material, e.g., copper or brass. The cylindrical piece has a thickness that is greater than the thickness of the first winding and an inner diameter dimensioned to fit around the first magnetic core. To fabricate the first winding, material is selectively removed from the cylindrical piece, e.g., by cutting or chemical etching, to form the first winding. For the embodiment in which the first winding comprises circular loops and jogs, the cylindrical piece may be cut or etched to form the circular loops and jogs of the first winding. The cylindrical piece may be cut using a laser cutter or mechanical tools. After the cylindrical piece has been cut or etched to form the first winding, the first winding is fitted around the first magnetic core and bonded to the first magnetic core, e.g., by an adhesive. Preferably, the first winding is thick enough at this stage to maintain its shape when fitted around the first magnetic core. After the first winding is bonded to the rotary shaft, the surface of the first winding is shaved or thinned down to obtain a desired outer diameter for the first winding. Thinning down the first winding to the desired outer diameter advantageously provides precise control of the outer diameter of the first winding and core assembly without requiring tight tolerances on the dimensions of the core.

The second winding is similarly fabricated from a hollow cylindrical piece of conductive material. Material is selectively removed from the cylindrical piece to form the second winding. The second winding is then bonded to the inner wall of the second magnetic core, and the surface of the second winding is thinned down to obtain the desired inner diameter for the second winding.

The space or gap between the outer diameter of the first winding and the inner diameter of the second winding determines the capacitive coupling between the two windings. Preferably, the gap is made small to provide greater capacitive coupling between the two windings. This requires precise control of the outer and inner diameters of the first and second windings, respectively. In the preferred embodiment, the first and second windings are thinned down to the desired outer and inner diameters, respectively, and hence the desired gap between the two windings. Machining the windings to obtain the desired gap between the windings is easier and more economical than machining the magnetic cores to obtain the desired gap because the magnetic cores are typically made of brittle ferrite material, which is more difficult to machine. It is also possible to obtain the desired gap by only thinning down one of the windings.

Figure 7:
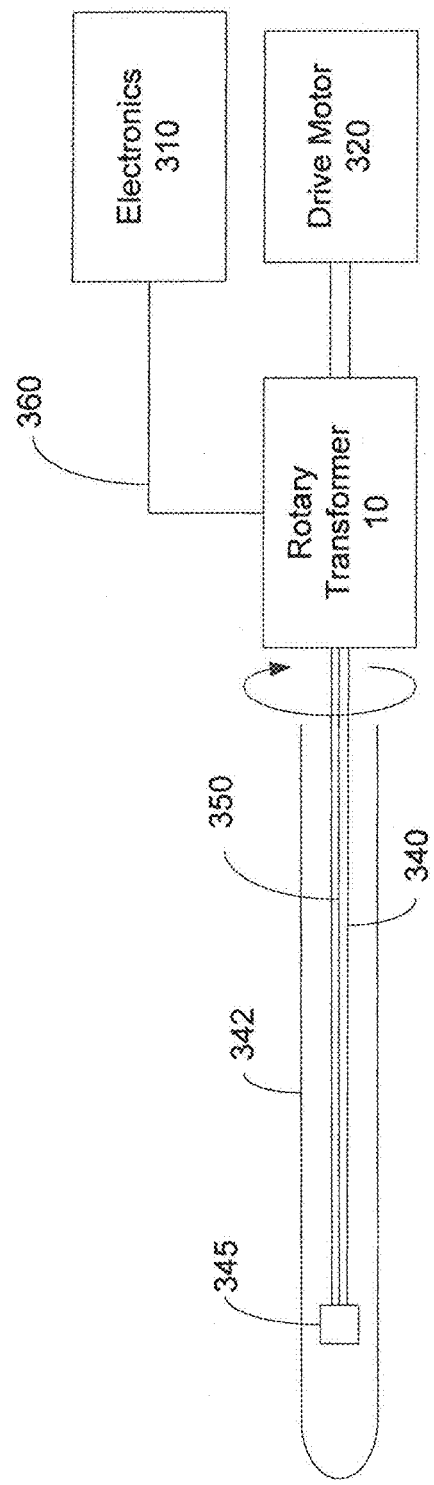
FIG. 7 is a diagram of a catheter system comprising a rotary transformer according to an example of the present invention.

FIG. 7 shows a diagram of an exemplary catheter system, in which a rotary transformer 10 can be used. The exemplary catheter system comprises a catheter body 342, a drive cable 340 disposed within a lumen of the catheter body 342, and an ultrasound transducer 345, e.g., piezoelectric element, attached to a distal end of the drive cable 340. The system further comprises the rotary transformer 10, a drive motor 320, and electronics 310 for processing signals to and from the transducer 345. The electronics may include filters, ultrasound signal processors, and the like. The rotary shaft of the rotary transformer is mechanically coupled between the drive cable 340 and the drive motor 320. For the exemplary rotary transformer shown in FIG. 4, the drive cable 340 is coupled to end 18 of the rotary shaft 15 and the drive motor 320 is coupled to end 16 of the rotary shaft 16. The rotary shall mechanically couples the drive motor 320 to the drive cable 340 enabling the drive motor 320 to rotate the drive cable 340, and hence the transducer 345 attached to the distal end of the drive cable 340. The system further comprises a transmission line 350 running through the drive cable 340 and electrically coupled between the transducer 345 and the first winding of the rotary transformer 10. The transmission line 350 rotates with the drive cable 340 and may comprise a coaxial cable, twisted pair wires, or the like. The transmission line 350 of the transducer 345 rotates relative to the transmission line 360 of the electronics 310, which is coupled to the second winding of the rotary transformer. The rotary transformer couples electrical signals between the two transmission lines 350, 360 enabling electrical communication between the rotating transducer 345 and the electronics 310. The electronics 310 need not be stationary. For example, the electronics 310 and the transducer 345 may both move longitudinally while the transducer 345 rotates relative to the electronics 310. The rotary transformer is not limited to use with rotating transducers and may be used in other applications where electrical communication is needed between rotating and non-rotating components in a system.

Multiple signals may be coupled by a rotary transformer. For example, the rotary transformer in FIGS. 1-4 may have multiple pairs of windings positioned along a common rotary shaft, where each pair of windings is used to couple one signal. In this example, the rotary transformer may comprise multiple non-rotating cores and a separate winding for each non-rotating core. The rotary transformer may further comprise multiple rotating cores on the common rotary shaft and a separate winding for each rotating core where the winding of each rotating core rotates within the winding of one of the non-rotating cores. The turn rations of the first and second windings may be different to provide impedance matching or voltage step-up or step-down. Further, the inner winding may be stationary while the outer winding rotates around the inner winding.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is new and desired to be protected by United States Letters Patent:

1. A, rotary transformer, comprising:
   a rotary shaft;
   a first magnetic core on the rotary shaft;
   a find winding wound around the first magnetic core, wherein the first winding comprisies a plurality of circular loops helically wound, wherein each of the plurality of circular loops is non-overlapping with each of the plurality of circular loops;
   a second magnetic core, wherein the second magnetic core is hollow;
   a second winding wound along an inner wall of the second magnetic core; and
   housing, wherein the second magnetic core and second winding are housed in the housing, the rotary Shaft, first magnetic core and first winding are rotatbly housed in the housing, and the first winding is rotatably disposed within the second magnetic cure.

2. The rotary transformer of clam 1, wherein the first winding comprises a substantially flat conductor wound around the first magnetic core.

3. The rotary transformer of claim 2, wherein the second winding comprises a substantially flat conductor wound along the inner wall of the second core.

4. The rotary transformer of claim 3, wherein the second winding comprises a plurality of circular loops helically wound, wherein each of the plurality of circular loops of the second winding is non-overlapping with each of the plurality of circular loops of the second winding.

5. The rotary transformer of claim 1, wherein the first winding is wound around a rotational axis of the rotary shaft.

6. The rotary transformer of claim 5, wherein the second winding is wound around the rotational axis of the rotary shaft.

7. The rotary transformer of claim 1, further comprising a first magnetic core end on the rotary shaft located adjacent to the first magnetic core, wherein the first magnetic core end has a larger outer diameter than the first magnetic core.

8. The rotary transformer of claim 7, further comprising a second magnetic core end located adjacent to the second magnetic core, wherein the second magnetic core end is hollow and has a smaller inner diameter than the second magnetic core.

9. The rotary transformer of claim 1, further comprising first and second magnetic core ends, wherein the first and second magnetic cores are located between the first and second magnetic core ends.

10. The rotary transformer of claim 1, wherein the first and second windings have a different number of turns.

11. A catheter system, comprising:
    a catheter body having a lumen;
    a work element rotatably received within the lumen of the catheter body; and
    a rotary transformed, comprising:
       a rotary shaft mechanically coupled to the work element;
       a first magnetic core on the rotary shaft;
       a first winding wound around the first magnetic core, wherein the first winding is electrically coupled to the work element and comprises a plurality of circular loops helically wound, wherein each of the plurality of circular loops is non-overlapping with each of the plurality of circular loops;
       a second magnetic core, wherein the second magnetic core is hollow;
       a second winding wound along an inner wall of the second magnetic core; and a housing, wherein the second magnetic core and second winding are housed in the housing, the rotary shaft, first magnetic core and first winding are rotatably housed in the housing, and the first winding is rotatably disposed within the second magnetic core.

12. The catheter system of claim 11, wherein the work element comprises an ultrasound transducer.

13. The catheter system of claim 11, wherein the first winding comprises a substantially flat conductor wound around the first magnetic core.

14. The catheter system of claim 11, wherein the second winding comprises a plurality of circular loops helically wound, wherein each of the plurality of the circular loops of the second winding is non-overlapping with each of the plurality of circular loops of the second winding.

15. The catheter system of claim 11, wherein the first winding is wound around a rotational axis of the rotary shaft.

16. The catheter system of claim 15, wherein the second winding is wound around the rotational axis of the rotary shaft.

17. The catheter system of claim 11, further comprising a drive motor mechanically coupled to the rotary shaft.

18. The catheter system of claim 11, wherein the first and second windings have a different number of turns.

19. A rotary transformer, comprising:
a rotary shaft;
a first magnetic cure on the rotary shaft;
a first winding wound around the first magnetic core;
a second magnetic core, wherein the second magnetic core is hollow;
second winding wound along an inner wall of the second magnetic core, wherein the second winding comprises a plurality of circular loops helically wound, wherein each of the plurality of circular loops is non-overlapping with each of the plurality of circular loops; and
a housing, wherein the second magnetic core and second winding are housed in the housing, the rotary shaft, first magnetic core and first winding are rotatably housed in the housing, and the first winding is rotatably disposed within the second magnetic core.

20. A catheter system, comprising:
a catheter body having a lumen;
a work element rotatably received within the lumen of the catheter body; and
the rotary transformer of claim 19, wherein the rotary shaft of the rotary transformer is mechanically coupled to the work element and the first winding of the rotary transformer is electrically coupled to the work element.

* * * * *